United States Patent
von Alfthan

(10) Patent No.: US 6,285,734 B1
(45) Date of Patent: Sep. 4, 2001

(54) METHOD FOR DETERMINING ELEMENT CONTENTS USING WAVE DISPERSIVE AND ENERGY DISPERSIVE X-RAY FLUORESCENCE ANALYSIS

(75) Inventor: Christian von Alfthan, Kauniainen (FI)

(73) Assignee: Outokumpu Oyj, Espoo (FI)

( * ) Notice: Subject to any disclaimer, the term of this patent is extended or adjusted under 35 U.S.C. 154(b) by 0 days.

(21) Appl. No.: 09/374,070

(22) Filed: Aug. 12, 1999

(30) Foreign Application Priority Data

Aug. 24, 1998 (FI) ........................................ 981810

(51) Int. Cl.$^7$ ................................................ G01N 23/223
(52) U.S. Cl. .................. 378/46; 378/44; 378/50; 378/45; 378/22; 250/308
(58) Field of Search ................... 378/46, 44, 50, 378/45, 22; 250/308, 310

(56) References Cited

U.S. PATENT DOCUMENTS

| | | | |
|---|---|---|---|
| 4,263,510 | * | 4/1981 | Ciccarelli et al. ................... 250/272 |
| 4,988,872 | * | 1/1991 | Nagatsuka et al. ................... 250/310 |
| 5,430,786 | * | 7/1995 | Komatsu et al. ........................ 378/45 |
| 5,497,407 | * | 3/1996 | Komatsu et al. ........................ 378/45 |

\* cited by examiner

Primary Examiner—Robert H. Kim
Assistant Examiner—Pamela R. Hobden
(74) Attorney, Agent, or Firm—Smith-Hill and Bendell

(57) ABSTRACT

The invention relates to a method for defining element contents contained by solid, liquid or slurry-like materials by means of an X-ray fluorescence method in an online analysis. According to the invention a combination of both the energy dispersive (3) and wave dispersive (2) X-ray fluorescence methods are applied in the method, so that by means of the energy dispersive method (3), there are measured such diffraction lines that are located essentially far from each other, whereas by means of the wave dispersive method (2), there are measured such diffraction lines that are located essentially near to each other as well as such diffraction lines where a high resolution and resulting accuracy and sensitivity are required.

8 Claims, 1 Drawing Sheet

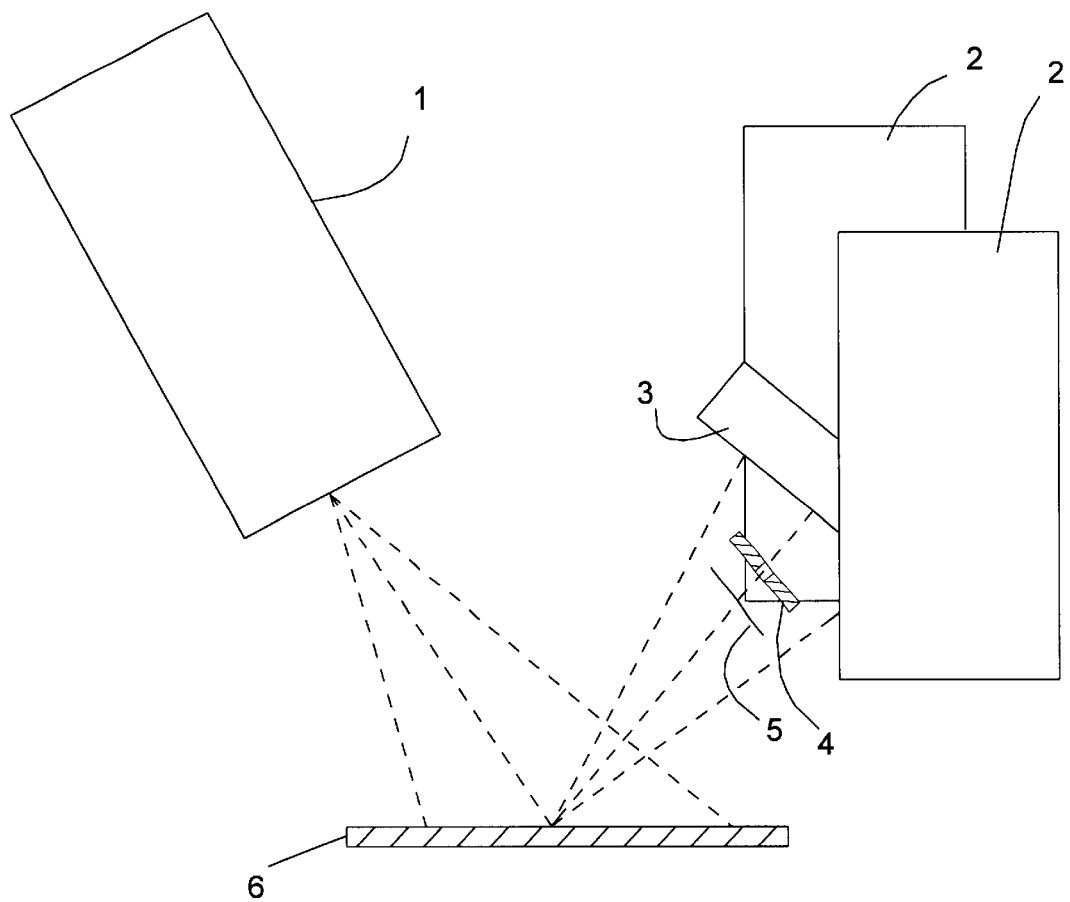

METHOD FOR DETERMINING ELEMENT CONTENTS USING WAVE DISPERSIVE AND ENERGY DISPERSIVE X-RAY FLUORESCENCE ANALYSIS

The present invention relates to a method for defining the element contents of solid, liquid or slurry-like materials by means of an X-ray fluorescence method.

X-ray fluorescence is an analysis method where the measuring arrangement includes an X-ray source, the material to be analyzed, a monochromator and a detector. While interacting with the radiation quantums emitted from the radiation source, the atoms of the material to be analyzed create a characteristic radiation with an energy typical of the element in question and with an intensity dependent on the element contents in said material.

As regards an analysis method based on X-ray fluorescence, there are known two alternative versions, i.e. a wave dispersive and an energy dispersive analysis, which differ in their detection methods. In wave dispersive analysis, the radiation emitted from the material is conducted to a monochromator, which separates a desired characteristic energy from the energy distribution of the incoming radiation on the basis of X-ray diffraction. The radiation separated by the spectrometer is detected and measured by means of a detector. By applying the wave dispersive method, there is achieved a high resolution, owing to which adjacent element lines can be separated, and the background behind the efficiency intensity remains relatively small. In a process control online analysis, the wave dispersive method has best sensitivity and accuracy, when the element contents in the material to be processed should be measured automatically and rapidly. When applying the wave dispersive method, each energy to be measured needs an individual monochromator, detector and measurement electronics.

The energy dispersive method utilizes the fact that the height of the electric pulses produced by the detector depends on the energy of the calculated radiation quantum. By electrically separating the calculated pulses on the basis of the pulse height, there is measured the frequency of the radiation quantums with a desired energy. With the energy dispersive method, several elements can be measured by one and the same detector, but the restriction in the total pulse frequency of the detector also restricts the element intensity and hence the achieved accuracy. Often the detector resolution is not sufficient to properly separate adjacent energy lines, which reduces particularly the measuring accuracy of the weaker line. Owing to poor resolution, there also is left more background behind the line than with the wave dispersive method. In total expenses, the energy dispersive method is economical in comparison with the wave dispersive method, but the sensitivity and accuracy of the energy dispersive method are clearly poorer than those of the wave dispersive method.

The object of the present invention is to eliminate some of the drawbacks of the prior art and to achieve an improved method for defining element contents, wherein the advantages of the energy dispersive and wave dispersive methods based on X-ray fluorescence in an online analysis of the material are advantageously combined. The essential novel features of the invention are apparent from the appended claims.

According to the invention, in the definition of element contents in a material by means of X-ray fluorescence, there are applied both the energy dispersive and the wave dispersive methods, so that by means of the energy dispersive method based on X-ray fluorescence, there is advantageously measured a plurality of diffraction lines, whereas the wave dispersive method based on X-ray fluorescence is applied only for those diffraction lines where high resolution and resulting accuracy and sensitivity are required. Because the combination of energy dispersive and wave dispersive methods according to the invention is dependent on the element combination to be analyzed, an advantageous combination of the energy dispersive and wave dispersive methods can be individually selected for each element combination. Because the elements and their mutual relations in the element combination to be analyzed remain essentially unchanged in an online analysis, the combination of the energy dispersive and wave dispersive methods according to the invention can be defined before beginning the online analysis.

The method of the invention can advantageously be applied so that on an unfiltered energy dispersive channel, there are measured the most intensive element lines, which are located far from each other, in which case the resolution of the detector is sufficient. If the diffraction line intensities are remarkably different, the ratio of the intensities can be advantageously adjusted by means of a filter arranged in front of the detector. Adjacent diffraction lines and such diffraction lines where a good signal to background ratio is needed owing to low intensity are measured by means of the wave dispersive method.

According to the invention, when treating diffraction lines requiring a high resolution by means of the wave dispersive method, the detector employed in the energy dispersive method in the online analysis is advantageously a proportional counter, cheaper than a semiconductor detector, which does not have to be cooled in order to make the counter function. The radiation intensity of the energy dispersive detector is advantageously reduced by means of a field stop placed in front of the detector, so that for the detector there is achieved an intensity corresponding to a pulse treatment speed depending on the material to be analyzed, advantageously below 12 kHz. The radiation intensity obtained in the energy dispersive detector is restricted by conducting the radiation to be measured onto the detector via a hole provided in a piece arranged in front of the detector, such as a piece of lead. Moreover, when the gas contained in the proportional counter and employed in the energy dispersive method is advantageously for example argon, with a pressure advantageously within the range of 5–7 bar, the effect of high energies in the measuring result, for instance the scattering possibly created at the top end of the wavelength range of the X-ray source spectrum, are removed from the treatment. Now a large part of the spectrum in this wavelength range passes through the detector without creating a pulse. On the other hand, the effect of low energies, such as the iron fluorescence caused by a large iron content, is removed from the treatment by placing a filter, having a thickness of 0.01–0.2 mm and made of aluminium, for example, in front of the detector.

The characteristics of the apparatus employed in the method according to the invention are essentially determined on the basis of the energy dispersive method. The intensity of the X-ray source, which is inversely proportional to the period of measurement, is dimensioned to be such that the wave dispersive method can be employed. While applying for instance 35 W as the X-ray source intensity, the resulting period of measurement is 2–3 minutes, whereas while applying the X-ray source intensity 300 W, the period of measurement is shortened to roughly 15 seconds.

In the method according to the invention, there is advantageously employed at least one channel for both the energy dispersive and the wave dispersive methods. In case two or more channels are used for one or both of the methods, the wave dispersive channels are generally tuned to different wavelengths, and the energy dispersive channels are tuned to different energy ranges.

The invention is explained in more detail below, with reference to the appended drawing, where a preferred embodiment of the invention is represented in a schematical illustration.

According to the drawing, the radiation created in the X-ray source 1 is conducted to the sample 6 to be analyzed. The sample 6 further emits X-ray fluorescence radiation, characteristic of the different elements, and the intensities of said radiations are measured both by means of an arrangement 2 operated on the basis of the wave dispersive method, where an individual monochromator, detector and measuring electronics are provided for each element, and by means of a detector 3 operated on the basis of the energy dispersive method, which detector is a proportional counter. In front of the energy dispersive detector 3, there is further arranged a field stop 4, which restricts the radiation intensity emitted from the sample 6, so that said intensity corresponds to the pulse treatment rate depending on the material to be analyzed, being advantageously below 12 kHz. Moreover, in front of the detector 3 there is provided a filter 5, which filters from the radiation for example an energy peak possibly created by a high iron content.

What is claimed is:

1. A method of determining presence of elements in a solid, liquid or slurry-like material in on-line analysis by an X-ray fluorescence method, comprising:

employing the energy dispersive method to measure diffraction lines that are widely spaced from each other and employing the wave dispersive method to measure diffraction lines that are relatively close to each other and to measure diffraction lines where high resolution and resulting accuracy and sensitivity are required, and reducing the radiation intensity received by the energy dispersive detector in order to achieve an advantageous pulse treatment rate by means of a field stop.

2. A method according to claim 1, wherein the step of reducing the radiation intensity received by the energy dispersive detector comprises providing a field stop in front of the energy dispersive detector.

3. A method according to claim 2, wherein the field stop is a piece of lead formed with a hole.

4. A method according to claim 1, comprising providing a filter in front of the energy dispersive detector for reducing the radiation intensity received by the energy dispersive detector in a selected energy range.

5. A method according to claim 4, wherein the filter is a piece of aluminum.

6. A method according to claim 1, comprising employing a proportional counter in the energy dispersive method.

7. A method according to claim 1, comprising employing at least two wave dispersive measurement channels tuned to different respective wavelengths.

8. A method according to claim 1, comprising employing at least two energy dispersive measurement channels tuned to different respective energy ranges.

* * * * *